United States Patent [19]

Shea et al.

[11] 4,007,528

[45] Feb. 15, 1977

[54] HIGH SPEED BONE DRILL

[76] Inventors: John J. Shea; Harry Phillips, both of P. O. Box 4360, Memphis, Tenn. 38104

[22] Filed: Oct. 22, 1975

[21] Appl. No.: 624,661

[52] U.S. Cl. .................................................. 32/26
[51] Int. Cl.² ......................................... A61C 1/08
[58] Field of Search .............. 279/1 B, 103, 75, 15; 32/26, 27

[56] References Cited

FOREIGN PATENTS OR APPLICATIONS 1,000,607  2/1952  France ..................................... 32/26
692,753    6/1953  United Kingdom ................... 32/26

*Primary Examiner*—Robert Peshock

[57] ABSTRACT

A high-speed, electric motor-contained bone drill has an elongate drive tube into which most of the length of a burr shank engages. Centrifugal discharge means at the inner end of the drive tube expell foreign matter, and a slide controls a chuck for the burr shank.

4 Claims, 7 Drawing Figures

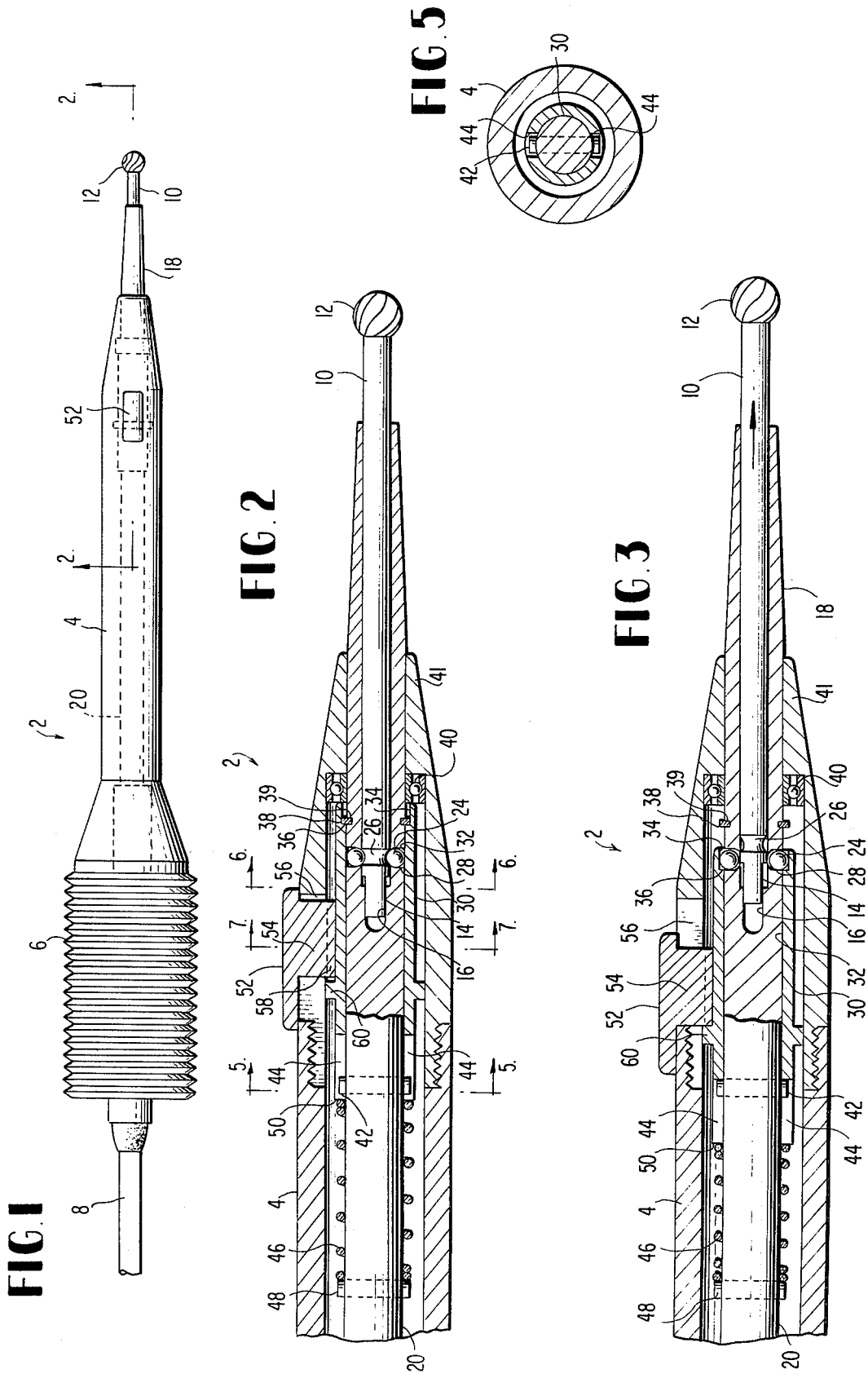

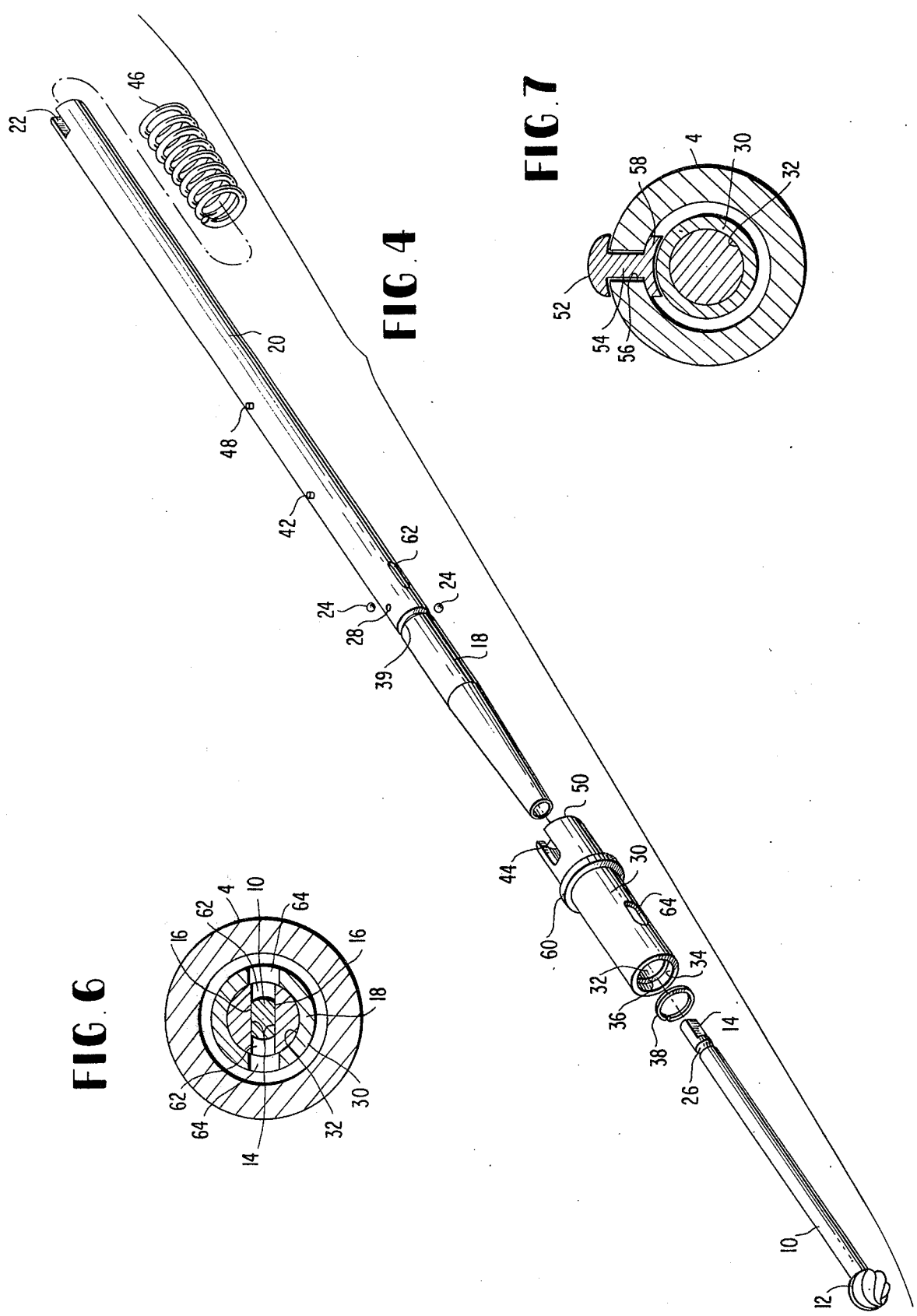

HIGH SPEED BONE DRILL

FIELD OF INVENTION

Chuck And Sockets, Side detent, Reciprocating sleeve.

PRIOR ART

Emrick U.S. Pat. No. 2,767,992; Ward et al. U.S. Pat. No. 3,367,727.

OBJECTS

In the performance of bone surgery, a comparatively small, high-speed drill with substantial torque is highly desirable. At speeds of, for example, 30,000 r.p.m. great care must be exercised in the design of the moving and bearing parts. Unbalance and bending or twisting tendencies of moving parts, and all possible rubbing friction must be avoided, lest the burr or bit vibrate and lest intolerable heat develop. The burrs must be exchangable by the surgeon by fast manipulation without having to distract his attention or observation from an operation in progress, and all possible risk or malengagement of a burr shank into the chuck of a tool must be avoided. The objects and results of this invention satisfy these requirements in a unique manner.

One object of the invention is to provide a drill having an elongate drive tube into which most of the length of a burr shank removably engages with a close sliding fit so that the burr shank is supported against bending over most of its length. A problem inherent in this sort of structure is that the parts are small and must fit together with great precision and, hence, any small bits of bone or other such matter which might have lodged upon the burr shank, or at the outer end of the drive tube, tend to get rammed into the inner end of the drive tube when a burr shank is inserted therein. Since the flatted inner end of the burr shank closely engages into a flat-sided socket at the inner end of the drive tube, virtually any foreign matter accumulated during a series of burr changes could readily interfere with the perfect fit of parts which is required at the inner end of the drive tube, and with the ball detent which prevents accidental dislodgement of the burr shank from the drive tube. To this end, it is now intended to provide radially-extending openings on opposite sides of the drive tube adjacent its inner end, whereby foreign matter lodged in the inner end of the tubular member is centrifugally expelled into the tool casing, from which it can be easily removed by subsequent cleaning, and where it will not interfere with the fit of parts at the inner end of the drive tube.

A further object is to provide a sliding sleeve controlled ball detent type chuck operated by a sliding finger piece, so that the detent can be released by one-finger manipulation. Because the sliding sleeve rotates with the drive tube upon which it is supported, and because the sliding finger piece is slidably mounted on the drill casing, which does not rotate, rubbing friction during normal drilling operation between the finger piece and the detent control sleeve must be avoided. Accordingly, it is proposed now to provide an arrangement where the finger piece does not ride against the detent control sleeve at any time other than when the finger piece is operated to slide the sleeve to a ball-detent releasing position.

These and other objects will be apparent from the following specification and drawings, in which:

FIG. 1 is a top plan view of a high speed bone drill;
FIG. 2 is a vertical cross section along the line 2—2 of FIG. 1, showing a burr shank locked in place;
FIG. 3 is a view similar to FIG. 2 showing the detent operated so as to release the burr shank;
FIG. 4 is an exploded view, in perspective, of the inner parts of the drive and detent assembly; and,
FIGS. 5, 6 and 7 are cross-sections along the lines 5—5, 6—6 and 7—7, respectively, of FIG. 2.

Referring now to the drawings, in which like reference numerals denote similar elements, the high speed bone drill 2 has a hollow casing 4 containing an electric motor (not shown) surrounded by cooling fins 6. A power cord 8 supplies electricity from a power supply to the motor. In this instance the motor is supplied with direct current and is reversible and capable of being controlled between comparatively high and intermediate speeds. Projecting forwardly from the distal end of the drill is the shank 10 of a burr 12. The inner end of shank 10 has an opposed pair of flats 14 which engage against spaced flats 16 formed in the inner end of an elongate tubular member 18 which is integral with a drive rod 20 which, in turn, is coupled via a non-rigid coupling member engaging in slot 22 to the motor.

Burr shank 10 is removably held in tube 18 by detent balls 24 which normally engage in an annular groove 26 in burr shank 10. Detent balls 24 reside in holes 28 in the tube and are normally trapped in annular groove 26 by sliding sleeve 30 whose inner surface 32 normally confines the detent balls (FIG. 2). However, the forward portion of the tube inner surface 32 has an enlargement 34 which terminates rearwardly in a shoulder 36. When sleeve 30 is slid to a rearward position (FIG. 3), detent balls 24 are free to move to an outer position wherein they no longer engage in annular groove 26. A snap ring 38 engaged in annular groove 39 on the exterior of drive tube 18 forms a stop against which shoulder 36 engages, thereby limiting the forward travel of sliding sleeve 30. A ball bearing 39 rotatably supports tubular member 18 in the nose 41 of casing 4. A cross pin 42 limits the rearward travel of a sliding sleeve 30 when the cross pin engages against the ends of slots 44 in the rear end of the sliding sleeve. The sleeve is resiliently pressed forwardly by an expansion spring 46 which is compressed between a cross pin 48 in drive rod 20 and the rear end surface 50 of the sliding sleeve.

Sliding sleeve 30 is moved from its normal FIG. 2 position to its burr shank-releasing position by a finger piece 52 which has an elongate flat shank 54 slidably engaging through a slot 56 in casing 4. Outward dislodgement of the finger piece and its shank is prevented by a curved base 58 which engages against the annular shoulder 60 on sliding sleeve 30. Thus when finger piece 52 is moved rearwardly, the rear surface of curved base 58 on shank 54 engages against shoulder 60 and pulls the sleeve rearwardly against the force of compression spring 46. It should be noted particularly in FIG. 2 that when sleeve 30 is in its foremost position, wherein shoulder 36 engages against snap ring 38, the curved base 58 on finger piece shank 54 is free to move away a small but nevertheless significant distance from the annular shoulder 60 on sliding sleeve 30, and thereby avoid rubbing against the shoulder 60 which would tend to produce heat and chatter.

Referring particularly to FIGS. 4 and 6, it should be noted that the flats 16 at the inner end of tubular member 18 are formed by a broach which is passed completely through the drive rod 20 at the inner end of the tubular member 18 so as to leave openings 62 which connect the space between the flats 16 and the outer surface of drive rod 20. Furthermore, sliding sleeve 30 is provided with opening 64 therethrough which register with openings 62. These openings 62 and 64 permit foreign matter which may have been rammed into the inner end of tubular member 18 by burr shank 10 to be expelled by centrifugal force into the hollow interior of casing 4. Because of the close fit between the burr shank 10 and member 18, even small amounts of foreign matter at this location can interfer with the operation of the device.

Although the tubular member 18 and drive rod 20 have been described with separate nomenclature, it will be understood that normally they would be machined out of a single piece. Additional bearings, not shown, are provided for the rear end of this piece. The forward end of the tubular portion 18, since it rotates with the burr shank, can be extended almost to the burr so as to support the burr shank against bending along almost its entire length.

The invention is not limited to the details disclosed and described hereinbefore, but is intended to cover all substitutions, modifications and equivalents within the scope of the following claims.

I claim:
1. A high speed drill comprising
a burr having an elongate shank,
a hollow casing,
a drive motor in said casing,
a drive member rotatably supported in said casing and drivingly connected at one end to said motor, said drive member having an elongate hollow tubular portion at the other end thereof for receiving said burr shank which slidably fits therein, means at the inner end of said hollow tubular portion for drivingly connecting said burr shank thereto,
a sleeve surrounding the drive member and slidable lengthwise thereon between first and second positions,
detent means engaging between said sleeve and said burr shank, said detent means being movable between one position in which the burr shank is held against endwise movement relative to said sleeve and another position in which the burr shank is released for endwise movement in said sleeve,
said sleeve in the first position thereof retaining said detent means in said one position and in the second position thereof releasing said detent means so that they are free to move to the other position thereof,
resilient means for urging said sleeve towards said first position, and a finger piece movably supported on said casing engageable with said sleeve for moving the same to said second position,
a rotary bearing member between the casing and the hollow tubular portion of the drive member, the elongate hollow tubular portion of said drive member projecting outwardly beyond said casing, and providing support for said burr shank along a substantial portion of its length.

2. A high speed drill as claimed in claim 1,
the means for drivingly connected said burr shank to said drive member comprising flats on the end of said burr shank and cooperating spaced flats on the inner side of said hollow tubular portion,
and aperture means extending radially through said hollow tubular portion and connecting the space between the spaced flats therein and the exterior of said hollow tubular portion, whereby to permit foreign matter to be centrifugally expelled from the inner end of said hollow tubular portion.

3. A high speed drill as claimed in claim 1,
said burr shank having an annular groove thereon,
said detent means comprising a plurality of balls loosely engaged in holes through said hollow tubular portion,
said sleeve having a first right cylindrical inner surface which, in the first position thereof confines said balls inwardly in said one position for engaging in the annular groove in the burr shank, said sleeve having a second right cylindrical inner surface larger than the first and which, in the second position thereof frees said balls for movement to the other position,
said sleeve being coupled to said hollow tubular portion for rotation therewith and having an annular shoulder thereon, said finger piece having thereon a surface which in the first position of said sleeve is spaced from said annular shoulder and which, upon movement of said finger piece, engages said shoulder for moving the sleeve to said second position.

4. A high speed bone drill as claimed in claim 3,
said sleeve surrounding the inner end of said hollow tubular portion and having aperture means therethrough registering with the aperture means in said hollow tubular portion, whereby to permit said foreign matter to be centrifugally expelled to the exterior of said sleeve.

* * * * *